United States Patent [19]

Kovalcheck

[11] Patent Number: 4,760,845
[45] Date of Patent: Aug. 2, 1988

[54] LASER ANGIOPLASTY PROBE
[75] Inventor: Steven W. Kovalcheck, San Diego, Calif.
[73] Assignee: HGM Medical Laser Systems, Inc., Salt Lake City, Utah
[21] Appl. No.: 3,209
[22] Filed: Jan. 14, 1987
[51] Int. Cl.$^4$ ............................................. A61B 17/36
[52] U.S. Cl. .................................. 128/303.1; 128/398
[58] Field of Search ........... 128/303.1, 303.13, 303.14, 128/303.15, 303.17, 397, 398; 219/230

[56] References Cited

U.S. PATENT DOCUMENTS

| | | | |
|---|---|---|---|
| 4,074,718 | 2/1978 | Morrison, Jr. | 128/303.14 |
| 4,519,390 | 5/1985 | Horn | 128/303.1 |
| 4,582,057 | 4/1986 | Auth et al. | 128/303.1 |
| 4,592,353 | 6/1986 | Kaikuzono | 128/303.1 |
| 4,662,368 | 5/1987 | Hussein et al. | 128/303.1 |

FOREIGN PATENT DOCUMENTS 8404879 12/1984 World Int. Prop. O. ....... 128/303.1

OTHER PUBLICATIONS

Abela, George S. et al., "Emerging Applications of Laser Therapy for Occlusive Vascular Disease" Card Review & Reports, 1985, 6(3) pp. 270-278.
Abela, George S. et al., "Hot Tip: Another Method of Laser Vascular Recanalization" Laser Surg. & Med., 1985, 5pp. 327-335.
Abela, George S. et al., "Laser Angioplasty with Angioscopic Guidance in Humans" J Am Coll Card, 1986, 8(1) pp. 184-192.
Abela, George S. et al., "Laser Revascularization: What are its Prospects?" J Card Med, 1983, 8(9) pp. 977-984.
Choy, Daniel S. J. et al., "Transluminal Laser Catheter Angioplasty" Am J Card, 1982, 50 pp. 1206-1208.
Cumberland, D. C. et al., "Percutaneous Laser Thermal Angioplasty: Initial Clinical Results with a Laser Probe in Total Peripheral Artery Occlusions" Lancet, 1986 pp. 1457-1459.
Dailuzono, Norio et al., "Artificial Sapphire Probe for Contact Photocoagulation and Tissue Vaporization with the ND:YAG Laser" Med Instr, 1985, 19(4) pp. 173-178.
Johnston, James H. et al., "Comparison of Heater Probe and YAG Laser in Endoscopic Treatment of Major Bleeding from Peptic Ulcers" Gastrointest Endosc, 1985, 31(3) pp. 175-180.
Lee, Garrett et al., "Dissolution of Human Atherosclerotic Disease by Fiberoptic Laser-Heated Metal Cautery Cap" Am Heart J, 107(4) pp. 777, 778.
McCowan, Timothy C. et al., "Human Percutaneous Laser Angioplasty" J Arkansas Med Soc, 1986, 82(12) pp. 594-596.

Primary Examiner—Lee S. Cohen
Attorney, Agent, or Firm—B. B. Olive

[57] ABSTRACT

A laser-energizable thermal probe comprising a probe assembly connected to the distal end of an optical fiber, the proximal end of the fiber being connectable to a source of laser energy. The probe assembly comprises a thermally conductive probe body, including a curvoidal tip and a neck portion, and contains an interior passage receiving the distal portion of the optical fiber. At the extremity of this interior passage may be disposed a mass of high emissivity material, to facilitate conversion of laser energy to thermal energy. The probe body is fixedly secured to the optical fiber by a helically wound conductive wire joined at its distal portion to the neck of the probe body and at its proximal portion to the optical fiber, to provide an extended heat transfer dissipation path for heat generated by the probe in use.

The disclosed device is useful for recanalization of occluded arteries, to remove intravascular plaque and thrombi therefrom.

21 Claims, 2 Drawing Sheets

LASER ANGIOPLASTY PROBE

BACKGROUND OF THE INVENTION

1. Field of the Invention

This invention relates to a laser-energizable device for heating tissue, having particular utility in angioplasty applications for the recanualization of occluded arteries by removal of intravascular plaque and thrombi therefrom.

2. Description of the Related Art

Occulsive heart disease, involving blockage of important coronary arteries, is a major cause of death among persons in the adult population. Even where death does not occur as a result of such disease, occluded arteries in the extremeties, liver, kidney, and brain nonetheless may lead to severe discomfort, loss of normal activity, and attenuation of the individual's quality of life.

The treatment of patients with occulsive arterial disease has generally been effected by two primary methods: pharmacological treatment for moderate arterial obstructions, and surgical treatments, including arterial bypass surgery and/or percutaneous transluminal angioplasty (PTA), in instances of severe stenosis.

Among the surgical options, bypass surgery is expensive, difficult, and depending on the location of the occluded artery, may involve traumatic procedures having high health risks and associated long recovery periods.

PTA, which has increased in popularity among vascular surgeons, involves the placement of a balloon catheter at the site of the constriction, and the subsequent widening of the arterial passage by inflation of the balloon. The benefits of PTA, as contrasted to bypass surgery, include less traumatic procedures, lower costs, respectable success in opening arterial occlusions, and relatively short patient recovery times. A primary disadvantage of PTA, however, is that the material causing the arterial blockage, e.g., arterial plaque or thrombi, is not removed but only pushed aside, with the possibility of future recurrent occlusions resulting from the continued accretion of plaque and/or thrombi to the displaced occluding deposits.

The utilization of laser irradiation for removal of the aforementioned arterial deposits has been advocated as a potentially effective means for the recanualization of occluded arteries. Such advocacy is based on the contention that intravascular laser irradiation can provide the same short-term benefits as PTA, with the additional advantage that the artery-occluding material is permanently removed.

The methods of laser irradiation which have been proposed include (1) direct laser irradiation, in which intravascular plaque and thrombi are removed through abalation, and (2) indirect laser irradiation in which laser energy is converted to thermal energy through the interaction of a laser beam with an absorptive, thermally conductive device, which when brought into close proximity or contact with plaque or thrombic complexes, dissolves, melts or evaporates the artery-blocking material.

Both of the above-discussed methods of laser irradiation involve the insertion of an optical fiber into the arterial channel, to function as a transmissive element for delivery of laser energy to the treatment site.

U.S. Pat. No. 4,519,390 to K. J. Horn discloses a laser catheter assembly including a unitary connector coupling the laser beam with an optical fiber. The patent, at column 5, line 36 to column 6, line 4, discloses to cool the optical fiber during use, by introducing a coolant such as carton dioxide gas into a port on the connector. From the port, the coolant passes through a bore in the connector surrounding the optical fiber, and flows through a length of catheter tubing associated with the fiber into a collet at the distal end of the fiber. The collet has a plurality of slots to allow flow of the coolant past the exposed tip of the optical fiber, and out of the distal end of the catheter assembly.

Although the catheter assembly of this patent has proven highly effective in use, the necessity of providing a separate source of coolant medium, and passing same through the collet past the exposed tip of the optical fiber at the treatment site, where high temperatures are generated, results in the introduction of the coolant medium to the arterial passage, from which it must be removed during treatment. As indicated, carbon dioxide gas is a preferred coolant, and the necessity for substantially completely removing such introduced gas from the arterial system is readily apparent, since any gas in the bloodstream after treatment may adversely affect the health and recovery prospects of the patient.

U.S. Pat. No. 4,592,353 discloses a medical and surgical contact laser probe for irradiating human tissue, including an optical fiber connected to a source of laser energy at one end and to a probe tip of laser transmissive material at its other end, with means for securing the transmissive material in the front position. A coolant medium, e.g., water or a gas (column 5, lines 1-3), is introduced into a catheter tubing surrounding the optical fiber, and laterally discharged at the distal end of the probe, to cool its tip. This device, then, is subject to the same deficiencies in use as the device of the previously described Horn patent.

U.S. Pat. No. 4,582,057 to D. C. Auth, et al., discloses a probe for heating tissue, comprising a probe body and a heat conductive portion forming an external heat transfer surface for contact with the tissue. A diode is mounted in the probe body in thermal contact with the heat conductive portion, so that electricity flowing through the diode generates heat which then is conducted to the heat transfer surface. The diode has a reverse breakdown voltage which is proportional to its temperature, and a power supply is connected to the diode through a suitable conductor. The power supply includes means for adjusting the power delivered to the diode, responsive to variations in the magnitude of the reverse breakdown voltage of the diode, to control the temperature of the probe. A plurality of water jets, which are circumferentially spaced about the body of the probe, direct water along the probe sidewalls in an axial direction to clean blood from the site to be cauterized.

The device of this patent requires the use of electrical source and supply means in conjunction with the thermoelectrical diode component. The device is comparatively complex, and requires electrical apparatus to be introduced into the patient's body. Such introduction of electrical apparatus may be hazardous, particularly in the treatment of coronary arteries of patients having implanted pacemakers, due to the electromagnetic interference generated by the probe, which may damage or interfere with electrocardial functions. Further, the device requires a water jet system, with the attendant disadvantages noted in connection with the art described hereinabove.

In addition to the devices described in the aforementioned patents, thermal probes have been developed for use in laser-energized optical fiber systems, comprising an ellipsoidal stainless steel probe tip formed with an integral neck portion, the proximal part of which is crimped onto the optical fiber. Such devices employ a longitudinal passage in the tip, radially displaced from its central axis, to accommodate a guide wire, and are commercially available in various sizes, as measured by the cross-sectional diameter of the probe tip (i.e., the minor axis dimension of the ellipsoidal tip), ranging from about 1.5 to 3 millimeters. The crimping application of the probe to the optical fiber in these devices provides a connection which however is susceptible to disengagement when the probe assembly is subjected to significant tensile forces during use. In addition to such susceptibility to disengagement of the tip from the optical fiber, these devices require a relatively high laser energy input intensity to effect the heating operation.

Accordingly, it would be a significant advance in the art to provide a laser-energized device, useful for performing tissue heating treatments such as angioplasty, which is cooled in a simple and efficient manner, without the introduction of any externally supplied coolant medium to the treatment site.

Accordingly, it is an object of the present invention to provide such a laser-energized device, which is conductively cooled and does not require the introduction of an externally supplied coolant medium to the treatment site.

It is another object of the present invention to specifically provide a laser angioplasty probe which is characterized by a high degree of structural integrity, even when subjected to significant tensile and/or compressive forces in the course of effecting treatment with the device.

It is a still further object of the invention to provide a laser-energized probe utilizing an optical fiber, in which laser energy is efficiently converted to thermal energy at a low input laser energy intensity, as compared with existing laser-energized thermal probes.

Other objects and advantages will be more fully apparent from the ensuing disclosure and appended claims.

SUMMARY OF THE INVENTION

In one aspect, the present invention relates to a laser-energizable thermal probe, comprising an optical fiber connectable at a proximal end to a laser energy source, for transmission of laser energy therethrough, and a probe assembly connected to the distal end of the fiber. The probe assembly comprises a thermally conductive probe body and a helically wound conductive wire as a joining means to secure the probe body to the optical fiber. The probe body comprises a curvoidal tip, and a neck portion joined to the tip and extending proximally therefrom. An interior passage in the probe body contains a distal portion of the fiber, with the distal end of the fiber in proximity to, and preferably within, the tip, whereby laser energy transmitted by the optical fiber to the probe body and converted to thermal energy is transmittable from the probe tip to a selected site in contact therewith. The helically wound thermally conductive wire is joined at its distal portion to the neck and at its proximal portion to the optical fiber, to provide an extended heat transfer dissipation path for heat generated by the probe assembly in use.

In another aspect of the laser-energizable thermal probe described above, a mass of a laser energy-absorptive, thermally conductive, high emissivity medium, is interiorly contained in a central portion of the curvoidal tip, in proximity to, and preferably in contact with, the distal end of the optical fiber.

In still another aspect of the invention as broadly described above, the helically wound conductive wire is welded at its distal portion to the probe body, and adhesively bonded at its proximal portion to the optical fiber. In a further aspect, such helically wound conductive wire may have successive turns thereof spot welded to one another, for enhanced mechanical integrity of the wire coil, preferably with finite spacings between the successive turns to permit pressure relief incident to heating of the probe assembly and associated portions of the optical fiber in use.

Another aspect of the invention relates to the provision of a "dressed" optical fiber, comprising a cladding of buffer and jacket layers, in which the fiber: (i) at its distal portion, as disposed in the probe body, is free of any cladding, (ii) proximally of such distal portion is covered only with the buffer layer for a predetermined length, and (iii) proximally of such predetermined length has the full cladding provided thereon. In this construction, the proximal portion of the helically wound conductive wire is secured to the jacket layer of the clad fiber, so that proximally of the (unclad) distal portion of the optical fiber in the probe body, and distally of the fully clad portion of the fiber, an annular space is provided between the buffer layer-covered optical fiber and the helically wound conductive wire.

Other aspects and features of the invention will be more apparent from the ensuing disclosure and appended claims.

DETAILED DESCRIPTION OF THE INVENTION, AND PREFERRED EMBODIMENTS THEREOF

Although the laser-energized device of the present invention is primarily described hereinafter as a "laser angioplasty probe," having specific utility for recanualization of occluded arteries, it will be apparent that the utility of the invention is not thus limited, but extends to any suitable heating operation in which the device may be usefully employed, including, but not limited to, heating, cauterizing, and removing tissue, etc.

In tissue-heating applications, the laser-energized probe of the present invention allows for the safe, effective, and efficient delivery to a tissue site of thermal energy, by transmission, and conversion into heat, of laser energy.

The probe assembly which is connected to the optical fiber in the device of the present invention comprises a thermally conductive probe body having a curvoidal tip at its distal portion. As used in such context, the term "curvoidal" refers to any three-dimensional shape having a predominantly convex, curved surface.

The curvoidal tip may thus for example be of a shape selected from those of the group consisting of spherical, spheroidal, and ellipsoidal shapes, e.g., an oblate spheroidal shape. Of the foregoing shapes, spherical tips are generally preferred in practice.

Figure 1:
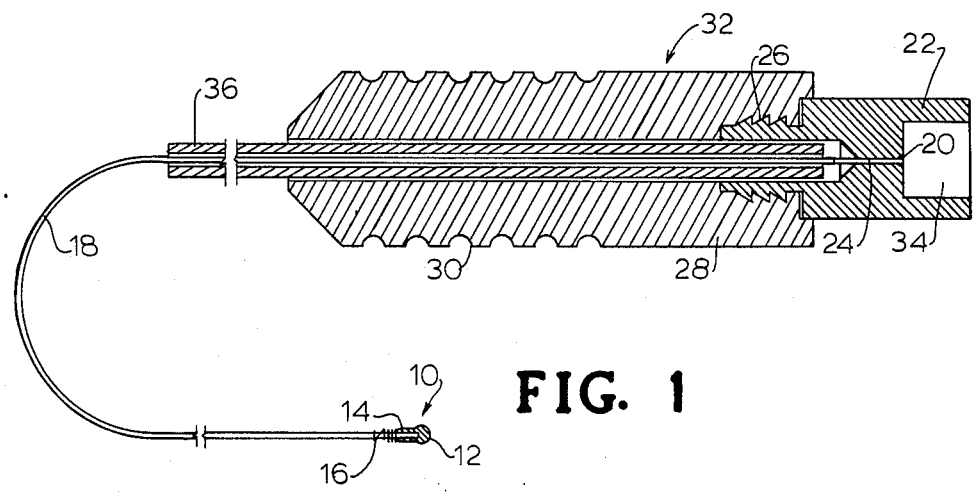
FIG. 1 is a partially sectioned elevation view of a laser angioplasty device, according to one embodiment of the present invention.

Referring now to the drawings, FIG. 1 shows a partially-sectioned elevation view of a laser-energized device according to one embodiment of the invention. In this construction, the probe assembly 10, comprising a thermally conductive probe body including a spherical tip 12 and a cylindrical neck 14, and the helically wound heat conductive wire 16, is disposed at the distal portion of an optical fiber 18, as described hereinafter in greater detail.

The optical fiber 18 may be of a conventional type, e.g., a quartz fiber having a bend radius of about 2 centimeters and a diameter of about 100–600 microns, fixed within a composite cladding providing both a mechanical support and a protective barrier for the otherwise brittle and easily damaged fiber. The composite structure of optical fiber and cladding, designated a "dressed optical fiber," is readily commercially available.

An illustrative dressed optical fiber which has been found useful in the practice of the present invention comprises (i) a 200 micron diameter high-purity quartz optical fiber core, (ii) a 240 micron diameter doped quartz clad layer providing a numerical aperture of 0.24 thereon, (iii) a 260 micron diameter buffer layer formed of HardClad non-optical polymer, commercially available from Ensign-Bickford Industries, Inc., Simsbury, Conn., and (iv) a 360 micron jacket formed of Tefzel®210 material, commercially available from E. I. duPont de Nemours & Co., Inc., Wilmington, Del. In this construction, the high density plastic buffer layer (iii) serves as a support medium uniformly contacting the doped quartz clad layer (ii) and permitting bending of the fiber, while the outer jacket (iv) protects the buffer layer and enhances the flexibility of the fiber. Each of the diameter values set forth above for the successive outer layers of the dressed fiber refers to outer diameter of the designated layer together with the associated core and any layer(s) interior to the designated layer. Of course, many other sizes, types and configurations of optical fibers may be used in the broad practice of the present invention without departing from the scope and substance thereof.

The optical fiber 18 in the vicinity of its proximal end 20 is disposed in a connector 22, in a central passage 24 thereof.

The connector 22 is threaded at its proximal portion 26 to mate with a correspondingly threaded plug body 28 having a ridged portion 30 for manual gripping. In such fashion the connector 22 and plug body 28 form a coupling assembly 32, in which the connector 22 provides a male fitting configured to be slidingly engageable with a corresponding female fitting (not shown) forming part of a laser apparatus. It will be appreciated that the connector 22 may be formed as a female fitting with the laser being provided with an appropriate corresponding male fitting. It will likewise be appreciated that other configurations of the coupling assembly may be employed to secure the optical fiber in proper alignment with a source of laser radiation emitted from a laser source, whereby laser energy is focused into the fiber.

The proximal portion of the connector 22 features a cavity 34 which is cylindrical in shape. Such cavity is provided so that if the laser beam is misaligned with the optical fiber and strikes the end of the connector, the laser beam will be somewhat attenuated by being out of focus. Further, the positioning of the proximal portion of the fiber in the passage 24 within the cavity has the advantage that the fiber will not be damaged during storage or handling.

Over the initial portion of its length extending distally from the coupling assembly, the dressed optical fiber 18 is sheathed in a covering 36 of a urethane, vinyl, rubber, or other suitable strain-releasing material, such sheath extending into the coupling assembly 32 comprising the plug body 28 and connector 22, in the manner shown.

The optical fiber 18 may be dressed as previously described along the major portion of its length, and undressed at its proximal portion, as positioned in the passage 24 of connector 22, as well as in the vicinity of the probe assembly, described hereinafter in greater detail.

Figure 2:
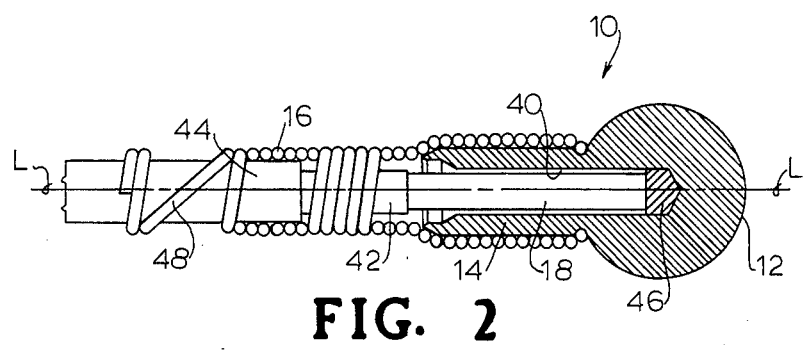
FIG. 2 is a partially-sectioned elevation view of the probe assembly portion of the device shown in FIG. 1, illustrating the details thereof.

FIG. 2 shows a detailed partially sectioned elevation view of the probe assembly of the FIG. 1 embodiment of the invention, together with its associated portion of the optical fiber.

The probe assembly 10 comprises a probe body including the spherical tip 12 and cylindrical neck 14. The probe assembly is formed of a suitable heat-conductive material, preferably a metal, with suitable illustrative metal materials including platinum, iridium and platinum/iridium alloys. Of the foregoing illustrative metals, platinum/iridium alloys are most preferred materials of construction.

The probe body comprising the spherical tip and cylindrical neck portions may be integrally formed, by any suitable method, such as casting, molding, machining, etc. It is also within the purview of the invention to provide a probe body of separately formed constituent tip and neck elements which are bonded or otherwise secured to one another, providing that the method of joining results in suitable mechanical integrity under use conditions. Nonetheless, as previously alluded to, the probe assembly is subjected to tensile and compressive forces in use, and to ensure the structural integrity of the probe assembly under such stress conditions, it generally is preferred in practice to provide the probe body as an integrally formed article.

As shown in FIG. 2, the probe body is formed with an interior passage 40 extending through the neck and into the tip of the body. The passage preferably is coaxial with the central axis L—L of the probe body, to centrally accommodate the optical fiber 18 in the passage so that uniform radial heat transfer is effected.

As previously indicated, the optical fiber may be dressed as shown in FIG. 2, in which the optical fiber 18 protrudes distally from that portion of the dressed fiber covered with only buffer layer 42. The buffer layer constitutes the sole covering of the optical fiber for a selected portion of its length, and proximally (i.e., rearwardly) thereof, a further outer jacket layer 44 is provided to form the composite cladding, the cladding being taken here as referring to the composite outer covering formed by the jacket and buffer layers together.

FIG. 2 shows a preferred feature of the present invention in the provision of a mass of laser energy-absorptive, thermally conductive, high emissivity material 46 in a cavity in the interior of the tip 12, as shown. As used herein, the term "high emissivity" means an emissivity of at least 0.80 (the emissivity of an ideal "black body" being taken as 1.0), consistent with high absorptivity and low reflectance of the laser energy impinged on the material. Preferably, the emissivity of the material is in the vicinity of 1.0. A preferred material for the high emissivity mass 46 is nuclear grade compressed graphite, although any other suitable high emissivity, high absorptivity, low reflectance material, responsive to laser energy to convert same into thermal energy for transmission to the tip 12, may be employed, e.g., carbon black, platinum oxide powder, etc.

The high emissivity mass 46 is disposed within the tip 12, preferably centrally therein, in proximity to the distal end of optical fiber 18. In such fashion, laser energy transmitted by the optical fiber impinges on the conductive core 46 and is converted to thermal energy which in turn is transmitted via conduction and radiation to the tip, whereby tissue or other material in contact with the external surface of the tip is subjected to intense heating. It will be appreciated that in some instances, the probe body may be constructed without the high emissivity core if the probe body is constructed of a suitable laser energy-absorptive material providing a sufficient rate of conversion of laser energy to thermal energy for the desired end use. Nonetheless, the use of a high emissivity core is generally preferred in practice as it provides a highly efficient laser energy/thermal energy conversion medium.

As previously discussed herein, a particular requirement of the probe assembly for employment in end use environments in which it is subjected to significant tensile and compressive stresses, is the provision of a high-integrity joining means for connecting the probe body to the optical fiber. It will be appreciated that in angioplasty applications, the separation of the probe body from the optical fiber is a serious event generally requiring immediate surgical intervention, and entailing potentially catastrophic occurrences if such separation is not immediately detected and corrected.

Accordingly, it is a specific feature of the present invention to provide a helically wound heat conductive wire as a joining means for coupling the probe body to the optical fiber. The helically coiled wire 16 may be joined at its distal portion by spot welding to the probe body. For example, the juncture of the tip and neck portions of the probe body may form a localized, circumferentially-extending cavity, and the first turn of the coiled wire may be disposed and spot welded or otherwise joined to the tip and/or neck portions of the probe body in the vicinity of this cavity. The helically wound coil may also be spot welded or otherwise permanently joined to the probe body along the length of the neck contacted by the coil, as necessary or desirable in the specific end use application.

As an alternative to spot welding, any other suitable method or means of bonding or fixedly joining the coiled wire to the probe body may be employed. Nonetheless, where the probe body is constructed of a metal material, it is preferred to employ welding as the joining method, since the thermal conductivity of the coil is not thereby adversely affected, such as would be the case if non-heatconductive bonding media were employed.

At its proximal end, the coil may feature one or more turns having an angular orientation, relative to the centerline of the probe assembly, greater than that of the other turns in the structure, as shown for example for coil strand 48 in FIG. 2. The proximal portion of the coil assembly is affixed to the dressed optical fiber, by adhesive bonding of the coil to the jacket 44 of the dressed fiber, or by any other suitable means or method of fixedly securing the proximal portion of the coil to the optical fiber.

In such fashion, there is provided by the helically wound thermally conductive wire 16 an extended heat transfer dissipation path for heat generated in the probe body in use. In other words, the probe body itself is formed of a heat conductive material which, in addition to transmitting heat to tissue in proximity therewith, conducts heat to the helically wound thermally conductive wire so that heat is transmitted along the successive turns of the coil in a proximal direction relative to the tip of the probe body. In this manner, a highly extended heat transfer surface area is provided, relative to the axial length of the coil.

To accommodate such heat transfer dissipation function, the helically wound coil is constructed of a thermally conductive material, which may be the same or different from the material of construction of the probe body. In practice, where the probe body is formed of the preferred platinum/iridium alloy, the same alloy has been advantageously used for construction of the helically wound heat conductive wire coil.

In general, the number of turns of the helically wound heat conductive wire in the coil is dependent on the length of wire required to allow the high temperature generated at the tip of the probe body to be diminished to a level below the melting point of the fiber's jacket and buffer layers, in order that the optical fiber and probe assembly are not damaged in use. This is highly critical where elevated temperatures, e.g., of as high as 1,000° C., are employed.

In such high temperature applications, the heat generated must be dissipated quickly and efficiently in order to avoid the aforementioned damage. This is readily accommodated by the helically wound coil in the probe assembly of the invention.

As an example, for a given temperature, e.g., 1,000° C., the helical wrapping of a heat conductive wire having a diameter equal to the wall thickness of a tubular heat-dissipative structure with an equivalent heat-dissipating capacity, provides the same temperature drop as the tubular structure over a substantially reduced axial distance. For example, in the probe assembly design shown in FIG. 2, the required axial length of a helically wound wire coil providing the safe thermal dissipation path (conduction only) is only 1/25 of the length of the corresponding tubular structure.

To increase the mechanical integrity of the helically wound heat conductive wire coil, successive turns thereof may be spot-welded to one another. While such welding of the turns in the coil does reduce the effective thermal conduction path provided by the coil, the heat dissipation benefits of the wire coils are so great in magnitude that even with turn-to-turn welding, the thermal conduction heat dissipation path provided by the coil is still substantially longer than that of a tubular heat dissipation structure.

Spot welding of adjacent turns in the coil is preferred, since it allows for finite spacing between weld points, where no turn-to-turn coil attachment exists. Such finite spacing between weld points provides openings in the coil structure which allow relief of pressure, such as may arise in operation due to heating and expansion of trapped air in the interior passage 40 of the tip 12.

As indicated, the proximal portion of the coil may be adhesively bonded to the jacket of the dressed fiber, using a suitable high temperature-resistant adhesive bonding medium, preferred materials having good thermal resistance at temperatures on the order of 100° C. and higher. The adhesive bonding medium may be any material meeting the applicable thermal stability and compatibility criteria for the intended end use environment. Preferred materials for angioplasty applications include biocompatible epoxies satisfying the criteria for PHS Class 6 materials, such as EE 0079/H0070 epoxy, commercially available from Hysol Division of The Dexter Corporation, Pittsburg, Calif., and EPO-TEK Type 301 epoxy, commercially available from Epoxy Technology, Inc., Billerica, Mass.

It is to be noted that the construction shown in FIG. 2 provides an anular space between the helically wound wire coil 16 and the buffer layer-coated optical fiber. In such manner, a "dead space" surrounds the optical fiber and protects it from the high temperatures associated with the radially adjacent portions of the circumferentially extending coil.

Figure 3:
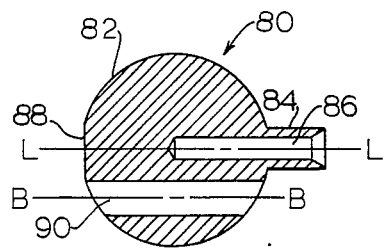
FIG. 3 is a sectional elevation view of a probe assembly body according to another embodiment of the invention, featuring a guide wire passage radially spaced from, and parallel to, the central axis of the body.

FIG. 3 shows a probe body 80 according to another embodiment of the present invention. The probe body comprises a generally spherical tip 82 and a cylindrical neck 84 integral therewith. As previously discussed, the probe body may be molded, cast, or machined from a metal such as platinum iridium alloy. The tip may have a cross-sectional diameter x, i.e., a diametral dimension, perpendicular to the longitudinal centerline L—L of the probe body, on the order of 2.5 millimeters, while the axial length of the probe body, as measured along the axial center line L—L, may be on the order of 3.2 millimeters. The diameter of the neck portion (outer diameter) may be on the order of 0.53 millimeters, and the interior diameter of passage 86, accommodating the insertion of the distal portion of the optical fiber, may be on the order of about 0.28 millimeters.

In general, the neck portion of the probe body is desirably constructed with a minimum diameter and length consistent with secure assembly to the optical fiber, and preferably with an outer diameter approximately the same as the diameter of the optical fiber jacket (see e.g., FIG. 2). The internal channel 86 extends preferably from the neck of the assembly to the center of the spherical tip and has a diameter which allows for a sliding fit with the optical fiber.

The FIG. 3 probe body may be constructed of a material such as platinum/iridium, which is preferred because of its high thermal conductivity, biocompatibility, and its resistance to corrosion and oxidation in a physiological environment. The exterior surface of the spherical tip is polished, preferably to a mirror finish, to minimize any possible adverse interactions between the probe body and its environment, e.g., abrasion of vascular walls when the probe assembly is utilized in angioplasty applications.

The tip 82 of the probe body shown in FIG. 3 is substantially spherical in shape, having only a small localized planar distal face 88 resulting from the machining operation by which the probe body is formed.

As a feature of the FIG. 3 embodiment, a guide passage 90 is provided, which is parallel to the central axis L—L of the probe, but radially displaced therefrom. This feature is more clearly shown in FIG. 4, which is a distal end elevation view of the probe body as shown in FIG. 3. The guide passage 90 accommodates a guide wire (not shown) which is inserted therethrough and defines a travel path along which the probe assembly may be directionally guided in use.

Figure 4:
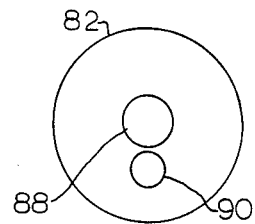
FIG. 4 is a distal view of the probe body of FIG. 3.

In an embodiment of the FIGS. 3 and 4 device having utility for angioplasty applications, the diameter of the guide passage 90 may be on the order of 0.44 millimeters, with the central axis B—B of this passage being at a radial distance of 0.64 millimeters from the central axis L—L of the probe body. The distal face 88 of the probe body in such embodiment may have a diameter of 0.50 millimeters.

Figure 5:
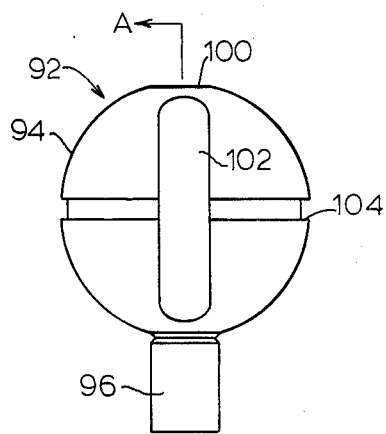
FIG. 5 is a top plan view of a probe body according to still another embodiment of the invention.
Figure 6:
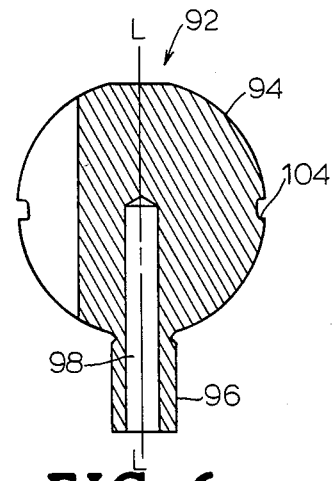
FIG. 6 is a sectional view of the FIG. 5 probe body, taken along line A—A of FIG. 5.
Figure 7:
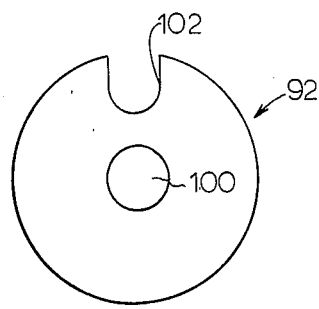
FIG. 7 is a distal end, elevation view of the probe body of FIG. 5.

FIGS. 5–7 show an alternative configuration for the probe body, according to another embodiment of the invention. FIG. 5 is a top plan view of such alternative probe body, FIG. 7 is a distal end elevation view of such probe body, and FIG. 6 is a sectional view thereof taken along line A—A of FIG. 5.

Referring to these drawings, there is shown a probe body 92 comprising a substantially spherical tip 94 integrally formed with a cylindrical neck 96, wherein the cross-sectional diameter of the tip may be on the order of 2.0 millimeters, and the outer diameter of the neck portion on the order of about 0.53 millimeters. The probe tip has a frontal planar face 100, with a diameter on the order of 0.5 millimeter.

As shown in FIG. 6, the probe body features a central axial passage 98, with a diameter which may be on the order of 0.28 millimeters, and with a length, as measured along axial centerline L—L, of about 1.83 millimeters. As in the other probe body embodiments previously described, the central passage provides a receptacle for mating with the distal end of the optical fiber, and accommodates at its innermost portion a mass of high emissivity material, which may suitably be of a type as previously described in connection with the FIG. 2 embodiment of the invention.

As shown in FIGS. 5 and 7, the tip 94 of the assembly features a concave recess 102, having a radius of curvature at the trough thereof, which is on the order of about 0.2 mm. The purpose of recess 102 is to accommodate a guide wire, the dimensions of the probe body 92 being sufficiently small that an interior guide wire passage, as used in the embodiment of FIGS. 3 and 4, cannot be employed.

Running circumferentially around the tip 94 in a direction generally perpendicular to the longitudinal axis L—L of the probe body, is a concave recess 104, the purpose of which is to accommodate a wire wrapping which overlies and thereby retains the guide wire in position in recess 102. Thus, a guide wire of 0.014 inch diameter may be retained in recess 102 by two overlying turns of 0.003 inch diameter platinum/iridium wire in recess 104, with each of the turns being welded to the tip at several discrete points.

The probe body embodiments shown in FIGS. 3–7 may usefully be employed in probe assemblies connectable to laser energy supply means in the manner generally described in connection with the probe assembly embodiment of FIGS. 1 and 2.

It will be appreciated that the dimensions of the various embodiments illustratively set forth hereinabove are for the purpose of facilitating understanding of the invention, and that other dimensions and dimensional relationships may be employed within the broad scope of the invention. In general, the cross-sectional diameter of the probe body's tip may range from about 1 to about 3 millimeters, with diameters between about 1 and about 2.5 millimeters being generally satisfactory for the majority of angioplasty applications.

Where the diameter of the tip is at the lower end of the aforementioned broad range, e.g., on the order of 1-2 millimeters in diameter, the construction of the general type shown in FIGS. 1 and 2 herein may be usefully employed. In this dimensional range, the probe body is highly guideable in character so that it does not require the use of guide catheters, as normally employed with arterial probes.

Where the diameter of the tip is at the upper end of the aforementioned broad range, i.e., on the order of 2-3 millimeters in diameter, the construction of the general type shown and described in connection with FIGS. 3-7 herein may be usefully employed, in which the tip is constructed with a passage accommodating a guide wire for directional guidance of the probe assembly along a predetermined travel path.

Such guide wire arrangement when employed is generally not the primary mode of guidance, however, since the flexibility of the optical fiber usually is sufficient to enable the device to readily traverse arterial passageways.

As indicated, for angioplasty applications of the laser-energized device of the present invention, it is generally desirable to provide the probe assembly tip with a highly-polished smooth surface, to facilitate travel of the probe assembly and heat transfer to tissue in contact therewith, and to enhance biocompatibility of the probe assembly so that the damage to non-treated tissue is minimized.

As also indicated, the probe assembly is preferably made of a highly conductive material, such as a platinum/iridium alloy. The probe assembly is preferably radiopaque, to permit the probe to be readily visualized with x-ray instrumentation.

In operation, the distal end of the laser angioplasty probe may be inserted into a guide catheter of a type which is conventionally employed and readily commercially available in a multitude of sizes and configurations. The probe, which by virtue of the short length of the probe assembly and its optical fiber connection is highly flexible in character, facilitating guideability of the device, is threaded through the guide catheter. The probe tip thus is guided to the tissue treatment site and positioned in contact with the arterial blockage. As indicated, x-ray visualization techniques can be employed to facilitate precise positioning of the tip when the probe assembly is constructed of a radiopaque material. The precise positioning of the probe assembly tip is further enhanced by the flexibility of the optical fiber, which as indicated may allow for insertion of the probe into the target blood vessel without the assistance of a guide catheter, particularly in the case of smaller diameter probe assemblies.

The proximal end of the optical fiber of the angioplasty device is attached to a suitable source of laser energy, for transmission of such energy through the optical fiber to the probe assembly. The beam emerging from the laser is focused into the proximal end of the optical fiber, and the laser energy emerging at the distal end of the fiber is absorbed either by the tip itself, or by a high emissivity core of material in thermal contact with the tip, as shown in FIG. 2. Regardless of whether the laser energy is transmitted directly, or indirectly (i.e., via conversion to thermal energy in a high emissivity core) to the probe assembly tip, the heat resulting from the conversion of such laser energy is conducted by the tip to its outer surface, for the production of intense localized heating.

As a result, arterial plaque and/or thrombi in contact with, or in close proximity to, the probe assembly tip, are subjected to such intense heating. The thermal conductivity of the probe assembly, and the curvoidal shape of its tip, facilitate a rapid uniform transfer of heat during laser activation, and provide a comparably rapid dissipation of heat and equilibration of tip temperature with intravascular temperature during cooling, i.e., laser deactivation.

During laser activation, heat traversing the tip of the probe assembly is also conducted proximally toward the optical fiber. The construction of the present invention avoids damage to the optical fiber and ensures the mechanical integrity of the probe assembly's connection to the optical fiber while maintaining a short overall tip and probe assembly length, by the provision of an extended heat dissipation path in the helically wound heat conductive wire coil serving as a means for connecting the probe body to the optical fiber.

Although specific features and embodiments of the invention have been described in detail, it will be appreciated that other embodiments, modifications, and variations are possible, and accordingly all such embodiments, modifications and variations are to be regarded as being within the spirit and scope of the present invention.

What is claimed is:

1. A laser-energizable thermal probe device, comprising:
   (a) an optical fiber having a proximal end portion connectable to a laser energy source, for transmission of laser energy therethrough to a distal end portion thereof; and
   (b) a probe assembly connected to said distal end portion of said optical fiber, and comprising:
      (i) a thermally conductive probe body including a curvoidal tip and a neck portion joined to said tip and extending proximally therefrom, with an interior passage in said probe body extending through said neck portion containing said distal end portion of said optical fiber, whereby laser energy transmitted by said optical fiber to said probe body and converted to thermal energy is transmittable by said tip thereof to a selected site in contact with said tip; and
      (ii) a helically wound thermally conductive wire having proximal and distal portions, said wire joined at its distal portion to said neck portion and at its proximal portion to said optical fiber, to provide an extended heat transfer dissipation path for heat generated by said probe assembly in use.

2. A device according to claim 1, wherein said neck portion is cylindrically shaped.

3. A device according to claim 1, wherein said interior passage extends into the curvoidal tip of said probe body.

4. A device according to claim 1, comprising a discrete mass of a laser energy-absorptive, high emissivity medium contacted by said distal end portion of said fiber and interiorly contained in a distal portion of said passage within said curvoidal tip.

5. A device according to claim 4, wherein said medium is compressed graphite.

6. A device according to claim 1, wherein said neck portion is cylindrically shaped and said interior passage is coaxial with said neck portion and extends into the curvoidal tip of said probe body, with a discrete mass of a laser energy-absorptive, high emissivity medium interiorly contained in a distal portion of said passage within said curvoidal tip, and with said optical fiber distal end in contact with said discrete mass.

7. A device according to claim 1, wherein said curvoidal tip is of a shape selected from those of the group consisting of spherical, spheroidal, and ellipsoidal shapes.

8. A device according to claim 1, wherein said curvoidal tip is spherically shaped.

9. A device according to claim 1, wherein the probe body is formed of a metal selected from the group consisting of platinum, iridium, and alloys thereof.

10. A device according to claim 1, wherein said helically wound conductive wire is formed of a metal selected from the group consisting of platinum, iridium, and alloys thereof.

11. A device according to claim 1, wherein said helically wound conductive wire is spot welded to said neck portion and adhesively bonded to said optical fiber.

12. A device according to claim 1, wherein successive turns of said helically wound conductive wire are spot welded to one another.

13. A device according to claim 13, wherein said successive turns of said helically wound conductive wire are in spaced relationship to one another between said spot welds, whereby interior and exterior pressures may readily be equalized by gas flow through the spaces between adjacent turns.

14. A device according to claim 12, wherein said optical fiber is cladded along its length, but not in the vicinity of said probe body, such that an annular space is provided proximally of said probe body in said vicinity, between the uncladded optical fiber and said helically wound conductive wire.

15. A device according to claim 1, wherein the curvoidal tip has a passage extending therethrough which is substantially parallel to, and radially spaced from, a central axis of said probe body, whereby said passage accommodates a guide wire for directional travel of the device along a path determined by the guide wire.

16. A device according to claim 1, wherein the probe assembly is radiopaque, whereby its location may be visualized in internal corporeal environments by x-ray detection.

17. A device according to claim 1, wherein the probe body has an axial length of from about 1 to about 5 millimeters.

18. A device according to claim 1, wherein said probe body curvoidal tip has a cross-sectional diameter of from about 1 to about 4 millimeters.

19. A device according to claim 1, wherein said probe body curvoidal tip has a cross-sectional diameter of from about 1 to about 2.5 millimeters.

20. A device according to claim 1, comprising a matable coupling joined to said optical fiber at said proximal end portion thereof, for connection of the device to said laser energy source.

21. A laser-energizable thermal probe device, comprising:
(a) an optical fiber having a proximal end portion connectable to a laser energy source, for transmission of laser energy therethrough to a distal end portion thereof; and
(b) a probe assembly connected to said distal end portion of said optical fiber, and comprising:
(i) a thermally conductive probe body including a curvoidal tip and a neck portion joined to said tip and extending proximally therefrom, with an interior passage in said probe body extending through said neck portion containing said distal end portion of said optical fiber, whereby laser energy transmitted by said optical fiber to said probe body and converted to thermal energy is transmittable by said tip thereof to a selected site in contact with said tip; and
(ii) a thermally conductive material formed with a distal portion mounted on said neck portion and a proximal portion mounted on said optical fiber to provide an extended heat transfer dissipation path for heat generated by said probe assembly in use.

* * * * *